(12) United States Patent
Tromp et al.

(10) Patent No.: US 6,486,129 B1
(45) Date of Patent: Nov. 26, 2002

(54) ANTITHROMBOTIC COMPOUNDS

(75) Inventors: Cornelia Maria Tromp, Ravenstein (NL); Johannes Egbertus Maria Basten, Afferden (NL); Constant Adriaan Anton van Boeckel, Oss (NL); Rogier Christian Buijsman, Oss (NL)

(73) Assignees: Akzo Nobel N.V., Arnhem (NL); University Leiden

( * ) Notice: Subject to any disclaimer, the term of this patent is extended or adjusted under 35 U.S.C. 154(b) by 0 days.

(21) Appl. No.: 09/719,841

(22) PCT Filed: Jun. 11, 1999

(86) PCT No.: PCT/EP99/04100
§ 371 (c)(1),
(2), (4) Date: Dec. 18, 2000

(87) PCT Pub. No.: WO99/65934
PCT Pub. Date: Dec. 23, 1999

(30) Foreign Application Priority Data

Jun. 17, 1998 (EP) ............................................. 98202037

(51) Int. Cl.[7] ........................ A61K 31/70; C07H 15/20; C07H 15/26; C07H 15/203
(52) U.S. Cl. .......................... 514/32; 514/25; 514/330; 514/517; 536/17.1; 536/17.4; 536/17.6; 536/17.9; 546/206; 562/36
(58) Field of Search .......................... 514/25, 32, 330, 514/517; 536/17.1, 17.4, 17.6, 17.9; 546/206; 562/36

(56) References Cited

FOREIGN PATENT DOCUMENTS

| EP | 0 236 163 | 9/1987 |
|---|---|---|
| EP | 0 513 543 | 11/1992 |
| EP | 0 558 961 | 9/1993 |
| EP | 0 649 854 | 4/1995 |
| EP | 0 818 459 | 1/1998 |

OTHER PUBLICATIONS

Steuber, W. et al., "Inhibition of thrombin by derivatives of the dipeptide aspartic acid–amidinophenylalanine" Chemical Structure Biology, 13th, 94, p. 643–5.

Walter, E., et al., "Transepithelial transport of four peptidomimetic thrombin inhibitors in monolayers of a human intestinal cell line (Caco–2)" Proc. Int. Symp. Controller Release ioact. Mater. vol. 21st, p. 712–13.

Primary Examiner—Peter O'Sullivan
(74) Attorney, Agent, or Firm—Mark W. Milstead; William M. Blackstone

(57) ABSTRACT

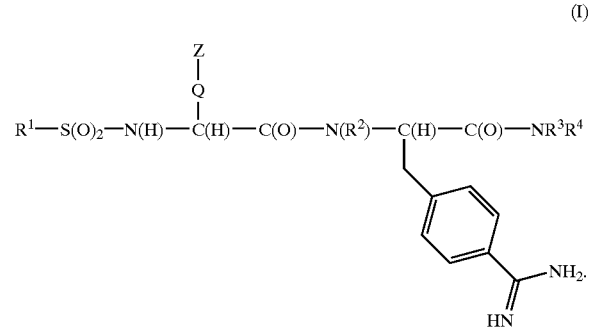

The present invention relates to compounds of formula (1), wherein $R^1$ is phenyl, naphthyl, 1,2,3,4-tetrahydronaphthyl, (iso)quinolinyl, tetrahydro(iso)quinolinyl, 3,4-dihydro-1H-isoquinolinyl, chromanyl or the camphor group, which groups may optionally be substituted with one or more substitutents selected from (1–8C)alkyl or (1–8C)alkoxy; $R^2$ and $R^3$ are independently H or (1–8C)alkyl; $R^4$ is (1–8C)alkyl or (3–8C)cycloalkyl; or $R^3$ and $R^4$ together with the nitrogen atom to which they are bonded are a nonaromatic (4–8)membered ring optionally containing another heteroatom, the ring optionally being substituted with (1–8C)alkyl or $SO_2$-(1–8C)alkyl; Q is a spacer having a chain length of 10 to 70 atoms; and Z is a negatively charged oligosaccharide residue comprising two to six monosaccharide units, the charge being compensated by positively charged counterions; or a pharmaceutically acceptable salt thereof or a prodrug thereof. The compounds of the invention have antithrombotic activity an can be used in treating or preventing thrombin-related diseases.

9 Claims, No Drawings

ANTITHROMBOTIC COMPOUNDS

The invention relates to new antithrombotic agents, a process for their preparation, pharmaceutical compositions containing the compounds as active ingredients, as well as the use of said compounds for the manufacture of medicaments.

Serine proteases are enzymes which play an important role in the blood coagulation cascade. Members of this group of proteases are for example thrombin, trypsin, factors VIIa, IXa, Xa, XIa, XIIa, and protein C. Thrombin is the final serine protease enzyme in the coagulation cascade. The prime function of thrombin is the cleavage of fibrinogen to generate fibrin monomers, which are cross-linked to form an insoluble gel. In addition, thrombin regulates its own production by activation of factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation. Since inhibitors of thrombin may have a wide range of therapeutical applications, extensive research is done in this area. Another important serine protease, factor Xa, catalyzes the conversion of prothrombin into thrombin.

In the development of synthetic inhibitors of serine proteases, and more specifically of thrombin, the benzamidine moiety is one of the key structures. It mimics the protonated side-chain of the basic amino acids Arg and Lys of its natural substrates. Compounds with this moiety have been studied extensively and repeatedly. A very potent representative of this type of thrombin inhibitors is the amino acid derivative Nα-(2-naphthylsulfonyl)-glycyl-4-amidinophenylaianinpiperidide (NAPAP) (Stürzebecher, J. et al., Thromb. Res. 29, 635–642, 1983). However, the profile of NAPAP is unattractive for therapeutical applications: for example, the compound has low thrombin specificity and is poorly soluble. Derivatives of NAPAP were subsequently prepared, such as the N-alkyl substituted derivatives disclosed in EP 0,236,163 or the glycopeptide derivatives described EP 0,558,961, Proc. Am. Pept. Symp., 13th (60LXAW); 94; pp. 643–5 (Stüber, W. et al., Pept.: Chem., Struct. Biol.,), Proc. Int. Symp. Controlled Release Bioact. Mater. (PCRMEY, 10220178); 94;Vol. 21 st; pp. 712–12 (Walter, E. et al.), and EP 0,513,543. However, although these derivatizations may have led to improvements of the pharmacological profile when compared to NAPAP, all such NAPAP-derived compounds are still active only as direct thrombin inhibitors and they have a restricted plasma half-life and a fast clearance (thus displaying their anti-thrombin activity only for a short period of time).

It has now been found that compounds of the formula (I)

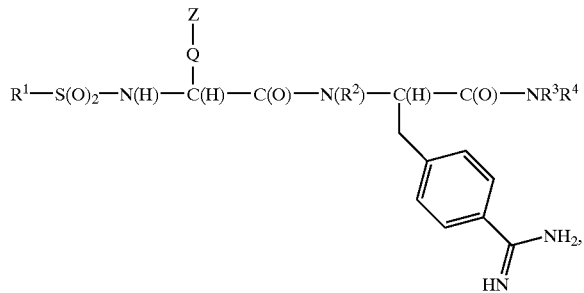

(I)

wherein

R$^1$ is phenyl, naphthyl, 1,2,3,4-tetrahydronaphthyl, (iso)quinolinyl, tetrahydro(iso)quinolinyl, 3,4-dihydro-1H-isoquinolinyl, chromanyl or the camphor group, which groups may optionally be substituted with one or more substituents selected from (1–8C)alkyl or (1–8C)alkoxy;

R$^2$ and R$^3$ are independently H or (1–8C)alkyl;

R$^4$ is (1–8C)alkyl or (3–8C)cycloalkyl;

or R$^3$ and R$^4$ together with the nitrogen atom to which they are bonded are a nonaromatic (4–8)membered ring optionally containing another heteroatom, the ring optionally being substituted with (1–8C)alkyl or SO$_2$-(1–8C)alkyl;

Q is a spacer having a chain length of 10 to 70 atoms; and

Z is a negatively charged oligosaccharide residue comprising two to six mionosaccharide units, the charge being compensated by positively charged counterions;

or a pharmaceutically acceptable salt thereof or a prodrug thereof are potent and highly versatile antitbrombotics. The compounds of the invention have antithrombin activity, but also the structure of the compounds may be selectively modified so that they have a tuneable mixed profile of both non-mediated, direct anti-thrombin (factor IIa) activity And antithrombin III (AT-III) mediated anti-Xa activity. The compounds of the invention thus are dual inhibitors. Compounds of the invention have a long plasma half-life and, as a result, they possess prolonged anti-thrombin activity compared to NAPAP or its above reported derivatives. Further, compounds of the invention may escape the neutralizing action of platelet factor 4 (PF4). Low toxicity is also an advantageous aspect of compounds of this invention.

Another type of dual inhibitors is disclosed in EP 0,649, 854. Contrary to the compounds of the present invention the conjugated saccharide compounds disclosed in that document display indirect, AT-III mediated anti-thrombin activity, in addition to AT-III mediated anti-Xa activity.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

The mixed profile of the compounds of the invention may be tuned by varying the nature of the oligosaccharide residue Z and the length of the spacer Q. A range of profiles is thereby available.

Any negatively charged oligosaccharide residue of 2 to 6 saccharide units is useable in the compounds of the present invention. Suitable compounds of the invention are compounds wherein Z is a sulfated or phosphorylated oligosaccharide residue. Preferably, the oligosaccharide residue Z is derived from an oligosaccharide which has per se AT-III mediated anti-Xa activity, such as the saccharides disclosed in EP 0,454,220 and EP 0,529,715. Particularly preferred oligosaccharide residues are pentasaccharide residues. Most preferably, Z has the formula (II)

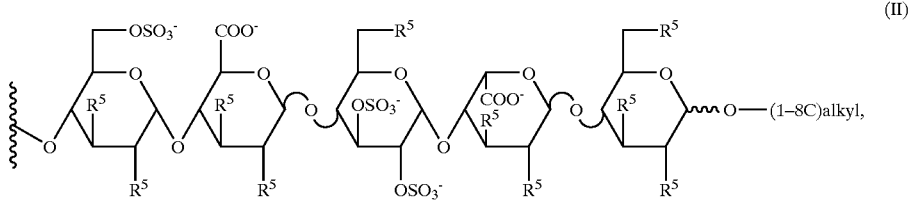

(II)

wherein $R^5$ is independently $OSO_3^-$ or (1–8C)alkoxy.

Further preferred compounds of the invention are compounds of formula I, wherein $R^1$ is phenyl, 4-methoxy-2,3,6-trimethylphenyl or naphthyl. In preferred compounds, $NR^3R^4$ represents the piperidinyl group. Preferably, $R^2$ is H.

The chemical structure of the spacer is of minor or no importance for the anti-thrombotic activity of the compounds of the invention, it may however not be completely rigid. Highly flexible spacers are more suitable than others. Further, for synthetic reasons some spacers are more appropriate than others. Suitable spacers that can easily be used have for example the formula (III):

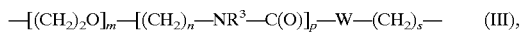
—[(CH$_2$)$_2$O]$_m$—[(CH$_2$)$_n$—NR$^3$—C(O)]$_p$—W—(CH$_2$)$_s$—  (III), wherein
W
is —[1,4-phenylene-NR$^3$—C(O)]$_q$—(CH$_2$)$_r$—S— or
—(CH$_2$)$_t$—S—(CH$_2$)$_u$—[O(CH$_2$)$_2$]$_v$—O—(CH$_2$)$_w$—C(O)—NR$^3$—;
and $R^3$ is independently H or (1–8C)alkyl;
m=1–12; n=1–8; p=0–4; q=0 or 1; r=1–8; s=1–8; t=1–8; u=1–8; v=1–12; w=1 8; the total number of atoms is 10–70; and the moiety —[(CH$_2$)$_2$O]$_m$— is the end with which Q is attached to Z.

Preferred spacers are the following:

—[(CH$_2$)$_2$O]$_5$—(CH$_2$)$_2$—NH—C(O)—CH$_2$—S—CH$_2$—;

—[(CH$_2$)$_2$O]$_5$—(CH$_2$)$_2$—NH—C(O)—CH$_2$—S—(CH$_2$)$_2$—[O(CH$_2$)2]$_3$—O—CH$_2$—C(O)—NH—(CH$_2$)$_4$—; and —[(CH$_2$)$_2$O]$_3$—(CH$_2$)$_2$—NH—C(O)-1,4-phenylene-NH—C(O)—CH$_2$—S—CH$_2$—.

In the description of the compounds of formula (I) the following definitions are used.

The term (1–8C)alkyl means a branched or unbranched alkyl group having 1–8 carbon atoms, for example methyl, ethyl, propyl, isopropyl, butyl, sec-butyl, tert-butyl, hexyl and octyl. Methyl and ethyl are preferred alkyl groups.

The term (1–8C)alkoxy means an alkoxy group having 1–8 carbon atoms, the alkyl moiety having the meaning as previously defined. Methoxy is a preferred alkoxy group.

The term (3–8C)cycloalkyl means a cycloalkyl group having 3–8 carbon atoms, being cyclopropyl, cyclobutyl, cyclopentyl, cyclohexyl, cycloheptyl or cyclo-octyl. Cyclopentyl and cyclohexyl are preferred cycloalkyl groups.

The spacer length is the number of atoms of the spacer, counted along the shortest chain between Z and the peptide part of the molecule, not counting the oxygen atom of the oligosaccharide Z which is connected to the spacer.

The term "prodrug" means a compound of the invention in which the amino group of the amidino-moiety is protected, e.g. by hydroxy or a (1–6C)alkoxycarbonyl group.

The compounds of the present invention are prepared by derivatizing NAPAP (or a NAPAP-analogue) at the glycine position with cysteine or lysine using methods generally known in the art, which compound subsequently (a) is coupled to a oligosaccharide-spacer residue or (b) is coupled to a spacer, which then is derivatized with a thiol group and subsequently is coupled to an oligosaccharide residue. Any suitable oligosaccharide may be used for this purpose, for example oligosaccharides known in literature (e.g. from EP 0,454,220 and EP 0,529,715, but not limited to these sources) or commercially available oligosaccharides. The oligosaccharides may be phosphorylated at an appropriate time by methods e.g. described by Buijsman, R. et al. (Abstracts of papers, 9th European Carbohydrate Symposium Utrecht 1997, Abstract A150). The coupling of the spacer to the oligosaccharide can for instance be performed by using the methods described in EP 0,649,854.

The peptide coupling, a procedural step in the above described method to prepare the compounds of the invention, can be carried out by methods commonly known in the art for the coupling—or condensation—of peptide fragments such as by the azide method, mixed anhydride method, activated ester method, or, preferably, by the carbodiimide method, especially with the addition of catalytic and racemisation suppressing compounds like N-hydroxysuccinimide and N-hydroxybenzotriazole. An overview is given in *The Peptides, Analysis, Synthesis, Biology*, Vol 3, E. Gross and J. Meienhofer, eds. (Academic Press, New York, 1981).

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group. Removal of the protecting groups can take place in different ways, depending on the nature of those protecting groups. Usually deprotection takes place under acidic conditions and in the presence of scavengers. An overview of amino protecting groups and methods for their removal is given in the above mentioned *The Peptides, Analysis, Synthesis, Biology*, Vol 3.

The compounds of the invention, which can occur in the form of a free base, may be isolated from the reaction mixture in the form of a pharmaceutically acceptable salt. The pharmaceutically acceptable salts may also be obtained by treating the free base of formula (I) with an organic or inorganic acid such as HCl, HBr, HI, H$_2$SO$_4$, H$_3$PO$_4$, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally. The exact dose and regimen of these compounds and compositions thereof will neccessarily be dependent upon the needs of the individual subject to whom the medicament is being administered, the degree of affliction or need and the judgment of the medical practitioner. In general parenteral administration requires lower dosages than other methods of administration which are more dependent upon absorption. However, the daily dosages are for humans preferably 0.001–100 mg per kg body weight, more preferably 0.01–10 mg per kg body weight. The medicament manufactured with the compounds of this invention may also be used as adjuvant in acute anticoagulant therapy. In such a case, the medicament is administered with other compounds useful in treating such disease states. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLES

Abbreviations used:
DMAP=N,N-dimethylaminopyridine
TEA=triethylamine
Z=benzyloxycarbonyl
Ac=acetyl
MMTr=monomethoxytrityl
Bn=benzyl
DCHA=dicyclohexylammonium
EDCI=1-(3-dimethylarninopropyl)-3-ethylcarbodiimide hydrochloride
HOBt=1-hydroxybenzotriazole
DiPEA=diisopropylethylamine
Pyr=pyridinyl
TEG=tetraethylene glycol
HEG=hexaethylene glycol
APA=amidinophenylalanine
Cys=cysteine The numbers of the compounds refer to the compounds on the formula sheets.

4-O-(4-O-(2,3,4,6-tetra-O-acetyl-α-D-glucopyranosyl)-2,3,6-tri-O-acetyl-α-D-glucopyranosyl)-2,3,6-tri-O-acetyl-α/β-D-glucopyranosyl trichloroacetimidate (4)

To a stirred solution of maltotriose (1) (2.0 g, 4.0 mmol) in pyridine (100 mL) was added acetic anhydride (6.2 mL, 65 mmol) and a catalytic amount of DMAP (0.79 g, 6.5 mmol). After 5 h the reaction mixture was poured into aqueous sodium hydrogencarbonate (1 M, 250 mL) and extracted three times with ethyl acetate (200 mL). The combined organic layers were dried on magnesium sulfate and concentrated in vacuo. The product was purified by column chromatography (light petroleum/ethyl acetate, 1/1 to 0/1, v/v) giving 2 as a white foam (91% yield, 3.5 g). Anomeric deacetylation was achieved by treatment of 2 (3.0 g, 3.1 mmol) with 0.1 M solution of hydrazine acetate in dimethylformamide (34 mL, 3.4 mmol) for 1 h. After concentration in vacuo the reaction mixture was diluted with ethyl acetate (50 mL), washed with sodium hydrogencarbonate (1 M, 3×25 mL), dried (magnesium sulfate) and concentrated. Purification by silica gel column chromatography (light petroleum/ethyl acetate, 3/2 to 1/0, v/v) gave 3 (92% yield, 2.7 g). Compound 3 (2.7 g, 3.1 mmol) was dissolved in dichloromethane (15 mL) and trichloroacetonitrile (1.7 mL) together with a catalytic amount of cesium carbonate (0.2 g, 0.62 mmol) were added. After 1 h the reaction mixture was filtered and the filtrate was concentrated under reduced pressure. Purification of the crude 4 by column chromatography (light petroleum/ethyl acetate/ TEA, 50/49/1 to 0/99/1, v/v/v) yielded pure 4 as white foam (1.9 g, 71%).

N-Benzyloxycarbonyl-1-aminohexaethylene glycol 4-O-(4-O-(2,3,4,6-tetra-O-acetyl-α-D-glucopymanosyl)-2,3,6-tri-O-acetyl-α-D-glucopyraosyl)-2,3,6-tri-O-acetyl-β-D-glucopyranoside (6)

A solution of donor 4 (0.69 g, 0.76 mmol) and acceptor 5 (0.31 g, 0.76 mmol) in dichloromethane (1.5 mL) was stirred for 1 h under a flow of argon in the presence of activated molecular sieves 4 Å (250 mg). The solution was cooled to −20° C. and a solution of trimethylsilyl trifluoromethanesulfonate (15 µL) in dichloromethane (0.6 mL) was added dropwise to the reaction mixture. After 10 min, TLC analysis (5% methanol in dichloromethane) showed the presence of one product. Solid sodium hydrogencarbonate (0.3 g) was added to the reaction mixture, which was stirred for 10 min and then filtrated. The filtrate was diluted with dichloromethane (50 mL), subsequently washed with aqueous sodium hydrogencarbonate (1 M, 2×25 mL), dried (magnesium sulfate), and concentrated in vacuo. The residue was chromatographed on silica gel (0–4% methanol in ethyl acetate) yielding pure 6 (0.57 g, 56% yield).

N-Benzyloxycarbonyl-1-aminohexaethylene glycol 4-O-(4-O-(α-D-glucopyranosyl)-α-D-glucopyranosyl)-β-D-glucopyranoside (7)

Compound 6 (0.57 g, 0.43 mmol) was treated with a solution of potassium tert-butylate (43 mg, 10 mg per mmol Ac) in methanol (15 mL). After 1 h TLC analysis (ethyl acetate/pyrdine/acetic acid/water, 5/7/4/1.6, v/v/v/v) indicate a complete conversion of 6 into 7. The reaction was neutralized with Dowex 50 WX4-W$^+$ resin. The resin was removed by filtration and the filtrate was concentrated under reduced pressure to afford 7 (0.37 g, 95% yield), which was used without further purification.

N-Benzyloxycarbonyl-1-aminohexaethylene glycol 4-O-(4-O-(α-D-glucopyranosyl-2,3,4,6-tetrakis-(dibenzylphosphate))-α-D-glucopyranosyl-2,3,6-tris(dibenzylphosphate))-β-D-glucopyranoside2,3,6-tris(dibenzylphosphate) (9)

A solution of 1H-tetrazole (54 mg, 0.77 mmol) in acetonitril (1 mL) was addded to a mixture of 7 (86 mg, 95 µmol)

and 8 (450 mg, 1.4 mmol) in acetonitril/dioxane (2/1, v/v, 2 mL). After stirring for 1 h at 20° C., the reaction mixture was cooled with an ice bath and tert-butylhydroperoxide (0.75 mL) was added. Stirring was continued for 45 min, afterwhich TLC analysis showed the presence of one main product. Purification by silica gel column chromatography (100/0 to 95/5, dichloromethane/methanol, v/v) furnished pure 9 (311 mg, 92% yield).

1-Aminohexaethylene glycol 4-O-(4-O-(α-D-glucopyranosyl 2,3,4,6-tetrakis phosphate)-α-D-glucopyranosyl 2,3,6-triphosphate)-β-D-glucopyranoside 2,3,6-triphosphate (10)

Compound 9 (311 mg, 87 μmol) was dissolved in tert-butanol/water (6/1, v/v, 20 mL) containing a few drops of acetic acid. The solution was stirred under a continuous stream of hydrogen in the presence of 10% Pd/C (100 mg). After 3 h the Pd/C catalyst was removed by filtration and the filtrate was concentrated in vacuo. Dowex 50 WX4Na$^+$ ion-exchange then furnished 10 (179 mg, 98% yield).

N-2-Naphtalenesulfonyl-S-4-monomethoxytrityl-(L)-cysteine (12)

To a stirred mixture of commercially available S-4-monomethoxytrityl-(L)-cysteine (11) (0.34 g, 1 mmol), dioxane (5 mL) and 10% aqueous sodium carbonate (5 mL) was added 2-naphtalenesulfonyl chloride (0.25 g, 1.1 mmol). After stirring for 1 h, the reaction mixture was acidified by addition of 5% aqueous citric acid (50 mL) and extracted with ethyl acetate (2×50 mL). The combined organic layers were dried (magnesium sulfate) and concentrated under reduced pressure. The crude product was chromatographed on silica gel (methanol/dichloromethane/triethylamine, 0/99/1 to 4/95/1, v/v/v) to yield 12 (76% yield, 0.44 g).

N-2-Naphtalenesulfonyl-S-2-pyridinesulfenyl-(L)-cysteine (14)

A solution of trifluoroacetic acid and triisopropylsilane in dichloromethane (1/1/18, v/v/v) was added to compound 12 (0.44 g, 0.76 mmol). After stirring for 20 min, the mixture was poured into water and extracted with dichlorometbane (2×50 mL). The combined organic layers were dried on magnesium sulfate and concentrated in vacuo. Traces of trifluoroacetic acid in the crude mixture were removed by coevaporation with toluene. The resulting free thiol 13 was redissolved in isopropanol (2.5 mL) and added dropwise to a solution of Aldrithiol™ (1.7 g, 7.6 mmol) in isopropanol/2 N aqueous acetic acid (1/1, v/v, 20 mL). After 1 h, TLC analysis indicated the reaction to be complete and the mixture was concentrated under reduced pressure. Traces of acetic acid in the residue were removed by coevaporation with toluene. The crude product was dissolved in acetone (10 mL) and to this solution dicyclohexylamine (0.3 mL) was added, afterwhich compound 14 precipitated from the reaction mixture as its DCHA-salt. The precipitate was isolated, dissolved in ethyl acetate (50 mL) and washed with 5% aqueous citric acid (2×30 mL). The organic layer was dried (magnesium sulfate) and concentrated under reduced pressure to afford pure 14 (55% yield, 0.25 g).

N(N(N$^\alpha$-2-Naphtalenesulfonyl-S-2-pyridinesulfenyl-(L)-cysteinyl)-(D,L)-4-amidinophenylalanyl) piperidine (16)

To a solution of N-((D,L)-4amidinophenylalanyl) piperidine dihydrochloride (15) (0.13 g, 0.39 mmol) and cysteine derivative 14 (0.16 g, 0.39 mmol) in dimethylformamide (2 mL) was added HOBt (58 mg, 0.42 mmol), EDCI (82 mg, 0.42 mmol) and N-ethylmorpholine (110 μL, 0.78 mmol). After stirring for 16 h, the mixture was diluted with dichloromethane (20 mL) and washed with water (2×10 mL). The organic layer was dried (magnesium sulfate) and concentrated in vacuo. The residue was purified by silica gel column chromatography (first 10%–20% methanol in dicblorometbane to remove impurities and then ethyl acetate/pyridine/acetic acid/water (16/7/1.6/4, v/v/v/v) to release product) and subsequently by gel filtration on Sephadex LH-20 (eluent: methanol/dichloromethane, 4/1, v/v) to yield homogeneous 16 (70%, 0.19 g).

Condensation Coupling of Maltotriose-decaphosphate 18 with Peptide 16

To a solution of maltotriose-decaphosphate 18 (21 mg, 9.8 μmol) in 0.1 M Na$_2$HPO$_4$ buffer (1.0 mL, pH 7.5) was added a solution of N-hydroxysuccinimidyl-2-bromoacetate in methanol (1 mL). After stirring for 2 h, the reaction mixture was applied on a Sephadex G25 column eluted with 10% acetonitril in water. The appropriate fractions were pooled and concentrated under reduced pressure at low temperature (25° C.) to yield compound 19. NAPAP analogue 16 (10 mg, 15 μmol) was dissolved in a mixture of methanol (1 mL) and 0.1 M Na$_2$HPO$_4$ buffer (0.75 mL, pH 7.0) degassed by passing through helium and by sonification. To this solution tributylphosphine (4.1 μL, 16 μmol) was added and the reaction mixture was stirred under an argon atmosphere. After 1 h HPLC analysis (Lichrospher® RP18-column) indicated a complete cleavage of the 2-pyridinesulfenyl group and a solution of compound 19 in dimethylformamide (0.25 mL) and 0.1 M Na$_2$HPO$_4$ buffer (0.50 mL, pH 7.0) was added to the reaction mixture. The mixture was stirred for 3 h, afterwhich the crude mixture was purified by gel filtration (Fractogel HW-40, eluent: 0.15 M TEAB). Concentration of the appropriate fractions and subsequent Dowex 50 WX-Na$^+$ ion-exchange gave after lyophilization homogeneous conjugate I (10.1 mg, 47% yield). The two diastereoisomers were separated by semi-preparative HPLC column chromatography (LiChrospher® RP-18 column, gradient: 17.5%–22.5% CH$_3$CN in 0.05 M aqueous TEAA) to give diastereoisomer I-a (retention time: 28.6 min) and diastereoisomer I-b (retention time: 33.0 min). The two isomers were desalted by gel filtration (Sephadex G-25 DNA-grade Superfine), transformed into the Na$^+$-form using Dowex 50 WX-Na$^+$ ion exchange resin.

Diastereoisomer I-a: $^1$H NMR (D$_2$O, 600 MHz, HH-COSY): maltotriose: (reducing end) 4.65 (bs, 1H, H1), 3.85 (m, 1H, H2), 4.35 (m, 1H, H3), 3.76 (m, 1H, H4); 5.50 (bs, 1H, H1'), 4.18 (m, 1H, H2'), 4.10 (m, 1H, H4'); (non-reducing end) 5.71 (bs, 1H, H1"), 4.09 (m, 1H, H2"), 4.45 (m, 1H, H3"), 4.15 (m, 1H, H4"); 3.95–3.84 (H5, maltotriose); spacer: 3.65–3.51 (m, 22H, OCH$_2$ HEG), 3.35 (m, 2H, CH$_2$NH$_2$), 3.15 (s, 2H, SCH$_2$(O)); peptide: 8.31 (s, 1H, H$_{arom}$ NAS), 8.06–7.67 (m, 6H, H$_{arom}$ NAS), 7.70, 7.17 (2×d, 4H, H$_{arom}$ APA, J=7.8 Hz), 4.28 (m, 1H, αCH APA), 3.91 (m, 1H, αCH Cys), 3.30–3.04 (m, 4H, CH$_2$N piperidine), 2.82–2.62 (m, 3H, βCH$_2$ Cys, βCH APA), 2.57 (m, 1H, βCH' APA), 1.45–1.25 (m, 6H, CH$_2$ piperidine);

ES-MS: [M−3H]$^{3-}$724.1, [M−2H]$^{2-}$1086.7.

Diastereoisomer I-b: $^1$H NMR (D$_2$O, 600 MHz HH-COSY): maltotriose: (reducing end) 3.80 (m, 1H, H2), 4.32 (m, 1H, H3), 3.89 (m, 1H, H4); 5.49 (bs, 1H, H1'), 4.22 (m, 1H, H2'), 4.11 (m, 1H, H4'); (non-reducing end) 5.70 (bs, 1H, H1"), 4.22 (m, 1H, H2"), 4.52 (m, 1H, H3"), 4.24 (m, 1H, H4"); 3.91–3.84 (H5, maltotriose); spacer: 3.63–3.52 (m, 22H, OCH$_2$ HEG), 3.35 (t, 2H, CH$_2$NH$_2$), 3.17 (AB, 2H, SCH$_2$(O)); peptide: 8.35 (s, 1H, H$_{arom}$ NAS), 8.07–7.65 (m, 6H, H$_{arom}$ NAS), 7.77, 7.22 (2×d, 4H, H$_{arom}$ APA, J=7.8 Hz), 4.62 (t, 1H, αCH APA, J$_{αCH,βCH}$=7.3 Hz), 4.05 (m, 1H, αCH Cys), 3.05–3.00 (m, 4H, CH$_2$N piperidine), 2.85–2.67 (m, 4H, βCH$_2$ Cys, βCH$_2$ APA), 1.88–1.24 (m, 6H, CH$_2$ piperidine);

ES-MS: [M−3H]$^{3-}$724.0, [M−2H]$^{2-}$1086.2.

N-Hydroxysuccinimidyl-14-S-2-pyridinesulfenyl-14-mercapto-3,6,9,12-tetraoxatetradecanoate (22)

Spacer 20 (0.75, 2.4 mmol) (P. Westerduin et al., Angew. Chem. Int. Ed. Engl. 1996, 35, 3, p331–333) and Aldrithiol™ (2.6 g, 12.1 mmol) was dissolved in dichloromethane (20 mL) and treated with n-butylamine (4 mL). After stirring for 2 h, the reaction mixture was concentrated in vacuo, redissolved in dichloromethane (50 mL) and washed with 5% aqueous citric acid (2×50 mL). The organic layer was dried and concentrated under reduced pressure. Silica gel column chromatography (methanol/acetic acid/dichloromethane, 0/1/99 to 6/1/93, v/v/v) of the residue yielded pure 21 (0.80 g, 88% yield). Compound 21 (0.80 g, 2.1 mmol) was dissolved in dichloromethane (10 mL) and N-hydroxysuccinimide (0.26 g, 2.3 mmol) and EDCI (0.45 mg, 2.3 mmol) were added to this solution. After 1 h, the reaction mixture was diluted with dichloromethane (50 mL), washed three times with ice water (20 mL), dried (magnesium sulfate) and concentrated to give 22 (0.98 mg, 98% yield,), which was used without further purification.

N$^ε$-tert-Butyloxycarbonyl-N$^α$-benzenesulfonyl-(L)-lysine (24)

Prepared as described for 12, using 23 and benzenesulfonyl chloride as starting materials. (0.86 g, 75% yield).

N$^ε$-(14-S-2-Pyridinesulfenyl-14-mercapto-3,6,9,12-tetraoxatetradecanoyl)-N$^α$-benzenesulfonyl-(L)-lysine (26)

Compound 24 (0.86 g, 2.2 mmol) was treated with 3 N hydrogen chloride in ethyl acetate. After 15 min the reaction mixture was concentrated in vacuo. Traces of acid in the residue were removed by coevaporation with toluene. The crude 25 was dissolved in a mixture of dioxane/water (4/1, v/v, 2.5 mL) and to this solution compound 22 (0.98 g, 2.1 mmol) and DiPEA (1.1 mL, 6.6 mmol) were added. After 1 h, the reaction mixture was diluted with dichloromethane (100 mL) and washed with 5% aqueous citric acid (2×50 mL). The organic layer was dried (magnesium sulfate) and concentrated in vacuo. The residual oil was purified by silica gel column chromatography (0–10% methanol/ethyl acetate) to give homogeneous 26 (0.95 g, 67% yield).

N(N(N$^ε$-(14-S-2-Pyrinesulfenyl-14-mercapto-3,6,9,12-tetraoxatetradecanoyl)-N$^α$-benzenesulfonyl-(L)-lysinyl)-(D,L)-4-amidinophenylalanyl)piperidine (27)

Prepared as described for 16, using 26 and 15 as starting materials. (87 mg, 70% yield).

Condensation Coupling of Maltotriose-decaphosphate 18 with Peptide 27 (II)

Prepared as described for I, using 18 and 27 as starting materials. Purification of the crude II was effected by semi-preparative HPLC (LiChrospher® RP-18 column). Subsequent desalting by gel filtration (Sephadex G-25 DNA-grade Superfine), transformation into the Na$^+$-form using Dowex 50 WX4-Na$^+$ ion exchange resin and lyophilization afforded pure II as a white fluffy solid (8.5 mg, 23% yield from 18).

$^1$H NMR (D$_2$O, 600 MHz, HH-COSY): maltotriose: (reducing end) 4.67 (m, 1H, H1), 4.07 (m, 1H, H2), 4.40 (m, 1H, H3), 4.06 (m, 1H, H4); 5.49 (bs, 1H, H1'), 4.24 (m, 1H, H2'), 4.66 (m, 1H, H3'), 4.10 (m, 1H, H4'); (non-reducing end) 5.73 (bs, 1H, H1"), 4.17 (m, 1H, H2"), 4.38 (m, 1H, H3"), 4.22 (m, 1H, H4"); 3.95–3.82 (H5, maltotriose); spacer: 4.03, 4.02 (2×s, 2H, OCH$_2$C(O)), 3.73–3.59 (m, 36H, OCH$_2$ TEG, HEG), 3.38 (t, 2H, CH$_2$NH$_2$), 3.27, 3.26 (2×s, 2H, SCH$_2$(O)), 2.75 (2×t, 2H, CH$_2$S); peptide: 7.81–7.52 (m, 5H, H$_{arom}$ BS), 7.79, 7.676, 7.42 7.41, (4×d, 4H, H$_{arom}$ APA), 4.87, 4.66 (2×t, 1H, αCH APA, J$_{αCH,βCH}$= 7.4 Hz), 4.07 (m, 1H, αCH Lys), 3.37–3.73 (m, 8H, εCH$_2$ Lys, βCH$_2$ APA, CH$_2$N piperidine), 1.96–1.46 (m, 12H, CH$_2$ piperidine, β/γ,δCH$_2$ Lys);

ES-MS: [M+3H]$^{3+}$801.2, [M+2H]$^{2+}$1200.8.

Partially Protected Pentasaccharide 30

Known pentasaccharide 29 (53 mg, 49 μmol) (R. C. Buijsman et al., Chem. Eur. J. 1996, 2, 12, p1572–1577) was dissolved in dimethylformamide (0.25 mL) and water (1 mL) and treated with N-(benzyloxycarbonyloxy)-succinimide (18 mg, 72 μmol) and N-ethylmorpholine (18.6 mL). After stirring for 15 min, TLC analysis (ethyl acetate/pyridine/acetic acid/water, 5/7/1.6/4, v/v/v/v) revealed the reaction to be complete and the reaction mixture was directly applied onto a RP-18 column, which was eluted with water/methanol (90/10 to 60/40). The appropriate fractions were pooled and concentrated to a small volume and applied on a Dowex 50 WX4-H$^-$ ion-exchange column in water. The eluate was concentrated in vacuo to yield pure 30 (54 mg, 91% yield).

Sulfated Pentasaccharide 32

Compound 30 (54 mg, 45 μmol) was dissolved in dimethylformamide (1 mL). Triethylamine sulfurtrioxide complex (0.51 g, 5 equiv for each hydroxyl group) was added and the mixture was stirred under a nitrogen atmosphere at 55° C. for 16 h. The mixture was subsequently cooled to 0° C. and aqueous sodium hydrogen carbonate was added (5 equiv for each eq. of triethylamine sulfirtrioxide complex). The mixture was stirred for 1 h, concentrated to a small volume and applied onto a Sephadex G-25 column, which was eluted with 10% acetonitril in water. The appropriate fractions were pooled and concentrated to a small volume, which was subsequently passed through a column of Dowex 50 WX4 (Na$^+$ form) eluted with water. The eluate was concentrated and redissolved in 0.2 N hydrogen chloride (1 mL) and allowed to stand for 16 h at 4° C. The reaction mixture was neutralized with 0.1 N sodium hydroxide and desalted on a Sephadex G-25 column and eluted with 10% acetonitril in water to afford homogeneous 31. Compound 31 was dissolved in tert-butanol/water (6/1, v/v, 20 mL) containing a few drops of acetic acid. The solution was stirred under a continuous stream of hydrogen in the presence of 10% Pd/C (100 mg). After 3 h the Pd/C catalyst was removed by filtration and the filtrate was concentrated in vacuo to furnish pure 32 (60 mg, 60% yield).

Condensation Coupling of Pentasaccharide 32 with Peptide 16

Pentasaccharide 32 (15 mg, 6.5 μmol) was dissolved in 0.1 M NaH$_2$PO$_4$ buffer (2 mL, pH 7.5 and to this solution was added sulfo-SIAB™ (16 mg, 33 μmol). After stirring 3 h in the dark, HPLC analysis (monoQ anion exchange) revealed the reaction to be complete and the crude 34 was purified on a Superdex 30 column (10% acetonitril in water). The appropriate fractions were pooled and concentrated in vacuo at low temperature (25° C). To a solution of NAPAP analogue 16 (9 mg, 14 μmol) in a mixture of methanol (1 mL) and 0.1 M Na$_2$HPO$_4$ buffer (0.75 mL, pH 7.0), degassed by passing through helium and by sonification before use, was added tributylphosphine (3.9 μL, 15 μmol). After stirring for 1 h under an argon atmosphere, HPLC analysis (Lichrospher® RP-18 column) indicated a complete cleavage of the 2-pyridinesulfenyl group. A solution of derivatized pentasaccharide 34 in dimethylformamide (0.25 mL) and 0.1 M $Na_2HPO_4$ buffer (0.50 mL, pH 7.0) was added and the mixture was stirred for 3 h. The crude product was applied onto a Sephadex G-50 column, which was eluted with 10% acetonitril in water. The appropriate fractions were pooled, concentrated to a small volume and desalted on a Superdex 30 column, which was eluted with 10% methanol in water. Concentration and lyophilization yielded conjugate III as a white solid (9 mg, 52% yield).

$^1$H NMR ($D_2O$, 600 MHz, HH-COSY): δ3.60, 3.53, 3.43 (3×s, 9H, $CH_3O_{E,G,H}$); ring D: 5.53 (m, 1H, H1), 4.15 (m, 1H, H2), 4.58 (m, 1H, H3), 3.56 (m, 1H, H4), 3.92 (m, 1H, H5), 4.26, 4.13 (2×m, 2H, H6, H6'); ring E: 4.70 (d, 1H, H1, $J_{1,2}$=8.1 Hz,), 4.21 (m, 1H, H2), 3.62 (m, 1H, H3), 3.92 (m, 1H, H4), 3.74 (m, 1H, H5); ring F: 5.39 (d, 1H, H1, $J_{1,2}$=3.8 Hz), 4.22 (m, 1H, H2), 4.56 (m, 1H, H3), 3.83 (t, 1H, H4, $J_{3,4}$=$J_{4,5}$=9.8 Hz), 4.12 (m, 1H, H5); ring G: 5.15 (bs, 1H, H1), 4.35 (m, 1H, H2), 3.76 (m, 1H, H3), 4.21 (m, 1H, H4), 4.80 (m, 1H, H5); ring H: 5.10 (d, 1H, H1, $J_{1,2}$=3.6 Hz), 4.31 (m, 1H, H2), 4.54 (m, 1H, H3), 4.21 (m, 1H, H4); spacer: 7.51, 7.53, 7.13, 712 (4×d, 4H, $H_{arom}$ SIAB), 3.73 (m, 2H, $CH_2CH_2NH_2$), 3.66 (m, 12H, $OCH_2$ TEG), 3.31 (m, 2H, $CH_2NH_2$); peptide: 8.27, 8.22 (2×s, 1H, $H_{arom}$ NAS), 7.98–7.60 (m, 6H, $H_{arom}$ NAS), 7.71, 7.64, 7.46, 7.44 (4×d, 4H, $H_{arom}$ APA), 4.60, 4.45 (2×t, 1H, αCH APA, $J_{\alpha CH,\beta CH}$= 6.6 Hz), 4.00, 3.97 (2×m, 1H, αCH Cys), 3.10–2.85 (m, 4H, $CH_2N$ piperidine), 2.82–2.70 (m, 3H, βCH$_2$ Cys, βCH APA), 2.61 (mn, 1H, βCH' APA), 1.55–1.15 (m, 6H, $CH_2$ piperidine);

ES-MS: [M–H]$^-$2680.6

Using similar methods, the following compounds are prepared:

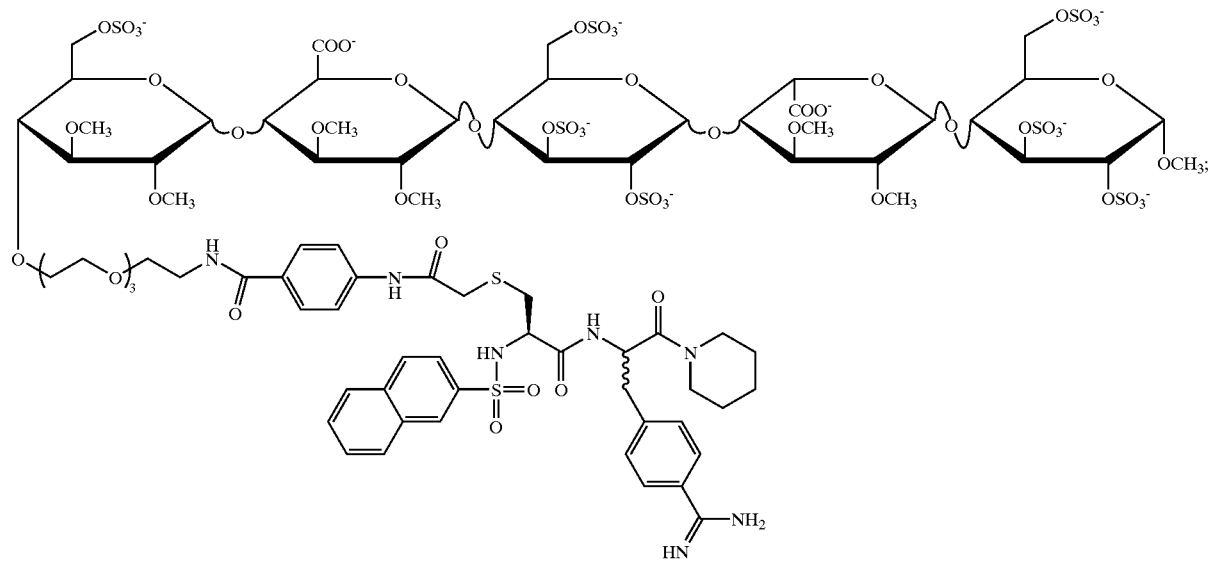

(IV)

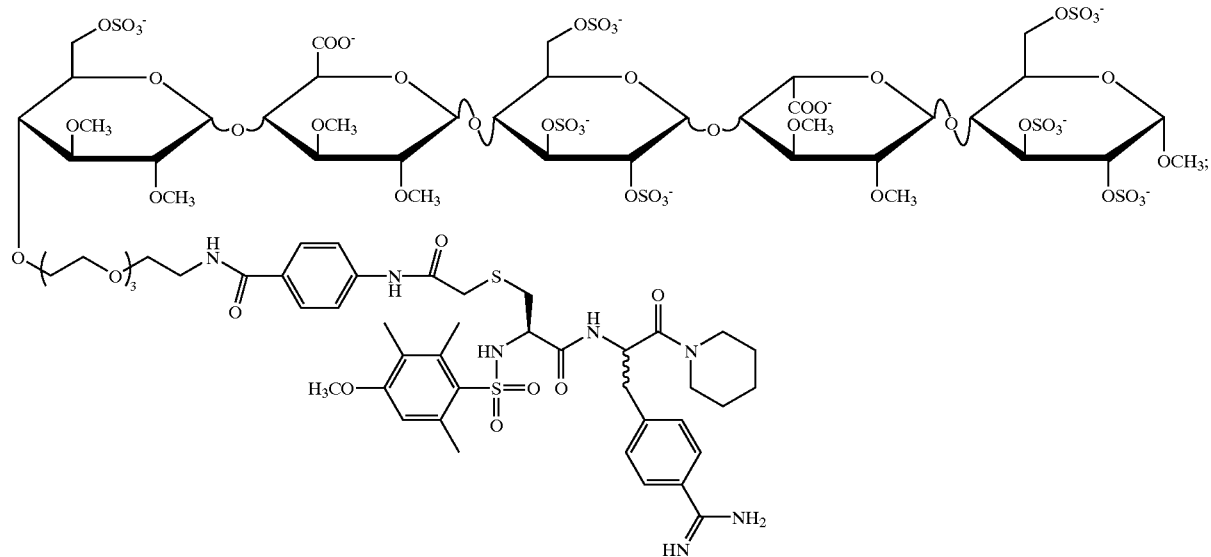

(V)

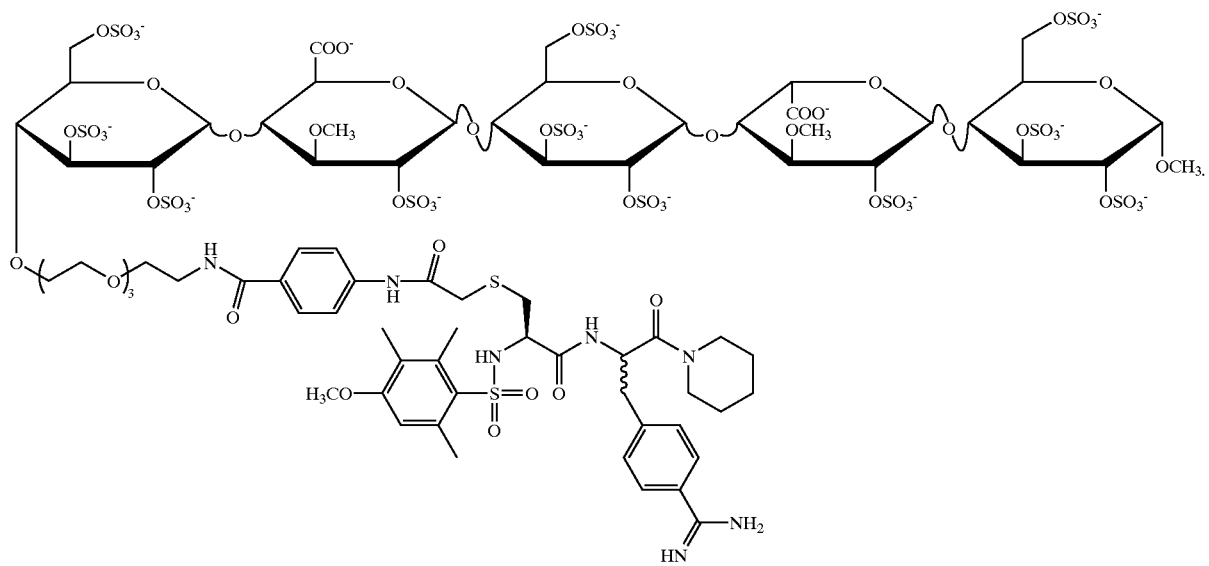

(VI)

The biological activities of the compounds of the present invention were determined by the following test methods.

I. Anti-thrombin Assay

Thrombin (Factor IIa) is a factor in the coagulation cascade.

The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the $IC_{50}$-value of a test compound.

Test medium: Tromethamine-NaCl-polyethylene glycol 6000 (TNP) buffer
Reference compound: I2581 (Kabi)
Vehicle: TNP buffer.
  Solubilisation can be assisted with dimethylsuiphoxide, methanol, ethanol, acetonitrfle or tert.-butyl alcohol which are without adverse effects in concentrations up, to 2.5% in the final reaction mixture.
Technique Reagents*
  1. Tromethamine-NaCl (TN) buffer
     Composition of the buffer:

| | |
|---|---|
| Tromethamine (Tris) | 6.057 g (50 mmol) |
| NaCl | 5.844 g (100 mmol) |
| Water to | 1 l |

The pH of the solution is adjusted to 7.4 at 37° C. with HCl (10 mmol·l$^{-1}$).
  2. TNP buffer
     Polyethylene glycol 6000 is dissolved in TN buffer to give a concentration of 3 g·l$^{-1}$
  3. S-2238 solution
     One vial S-2238 (25 mg; Kabi Diagnostica, Sweden) is dissolved in 20 ml TN buffer to give a concentration of 1.25 mg·ml$^{-1}$ (2 mmol·l$^{-1}$).
  4. Thrombin solution
     Human thrombin (16 000 nKat·vial$^{-1}$; Centraal Laboratorium voor Bloedtransfusie, Amsterdam, The Netherlands) is dissolved in TNP buffer to give a stock solution of 835 nKat·ml$^{-1}$.
     Immediately before use this solution is diluted with TNP buffer to give a concentration of 3.34 nKat·ml$^{-1}$.
All ingredients used are of analytical grade
For aqueous solutions ultrapure water (Milli-Q quality) is used.
  Preparation of test and reference compound solutions
     The test and reference compounds are dissolved in Milli-Q water to give stock concentrations of $10^{-2}$ mol·l$^{-1}$. Each concentration is stepwise diluted with the vehicle to give concentrations of $10^{-3}$, $10^{-4}$ and $10^{-5}$ mol·l$^{-1}$. The dilutions, including the stock solution, are used in the assay (final concentrations in the reaction mixture: $3·10^{-3}$; $10^{-3}$; $3·10^{-4}$; $10^{-4}$; $3·10^{-5}$; $10^{-5}$; $3·10^{-6}$ and $10^{-6}$ mol·l$^{-1}$, respectively).
  Procedure
     At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).
     All data are collected in an IBM personal computer using LOTUS-MEASURE. For each compound concentration (expressed in mol·l$^{-1}$ reaction mixture) and for the blank the absorbance is plotted versus the reaction time in min.

Evaluation of responses: For each final concentration the maximum absorbance was calculated from the assay plot. The $IC_{50}$-value (final concentration, expressed in $\mu mol \cdot l^{-1}$, causing 50% inhibition of the maximum absorbance of the blank) was calculated using the logit transformation analysis according to Hafner et al. (Arzneim.-Forsch./Drug Res. 1977; 27(II): 1871-3).

Antithrombin Activity

| Example | $IC_{50}$ (mol · $l^{-1}$) |
|---|---|
| I (one diastereomer) | $2 \times 10^{-7}$ |
| II | $8 \times 10^{-6}$ |
| III | $3.5 \times 10^{-7}$ |

II. Anti-factor Xa Assay

Activated Factor X (Xa) is a factor in the coagulation cascade. The anti-Xa activity of compounds of the present invention was assessed by measuring spectrophotometrically the rate of hydrolysis of the chromogenic substrate s-2222 exterted by Xa. This assay for anti-Xa activity in a buffer system was used to assess the $IC_{50}$-value of the test compound.

In general the followed procedure and test conditions were analogous to those of the anti-thrombin assay as described above. Differences are indicated below.

Reference compound: benzamidine
Vehicle: TNP buffer.
    Solubilisation can be assisted with dimethylsulphoxide, methanol ethanol, acetonitrile or tert.-butyl alcohol which are without adverse effects in concentrations up to 1% (for DMSO) and 2.5% (for the other solvents) in the final reaction mixture.

Technique Reagents*
  3. S-2222 solution
    One vial S-2222 (15 mg; Kabi Diagnostica, Sweden) is dissolved in 10 ml water to give a concentration of 1.5 mg·$ml^{-1}$ (2 mmol·$l^{-1}$).
  4. Xa solution
    Bovine Factor Xa Human (71 nKat·$vial^{-1}$; Kabi Diagnostica) is dissolved in 10 ml TNP buffer and then further diluted with 30 ml TNP buffer to give a concentration of 1.77 nKat·$ml^{-1}$. The dilution has to be freshly prepared.

Procedure
    Instead of the S-2238 solution (in anti-thrombin assay), the above S-2222 solution is added to each well in this assay.

Anti-factor Xa activity

| Example | U/mg |
|---|---|
| III | 885 |

FORMULA SHEET 1

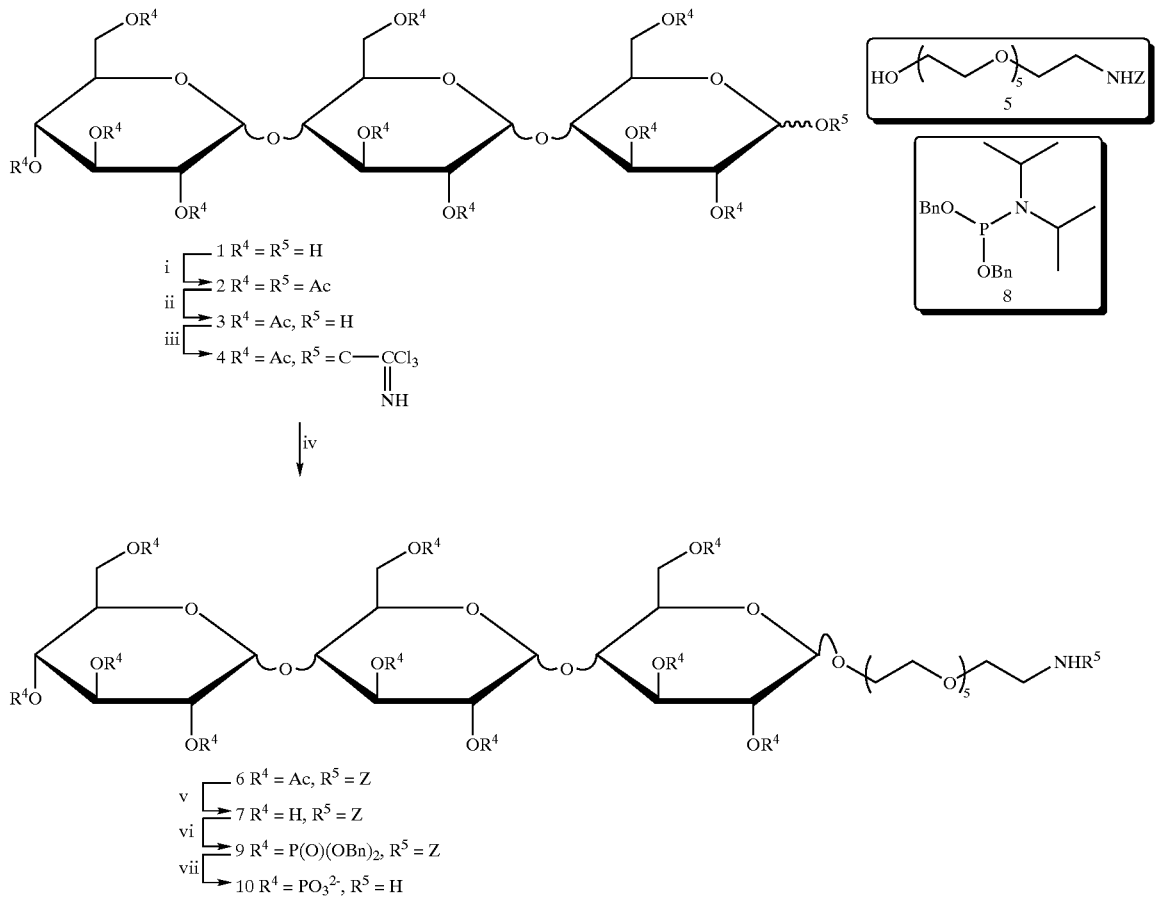

FORMULA SHEET 2
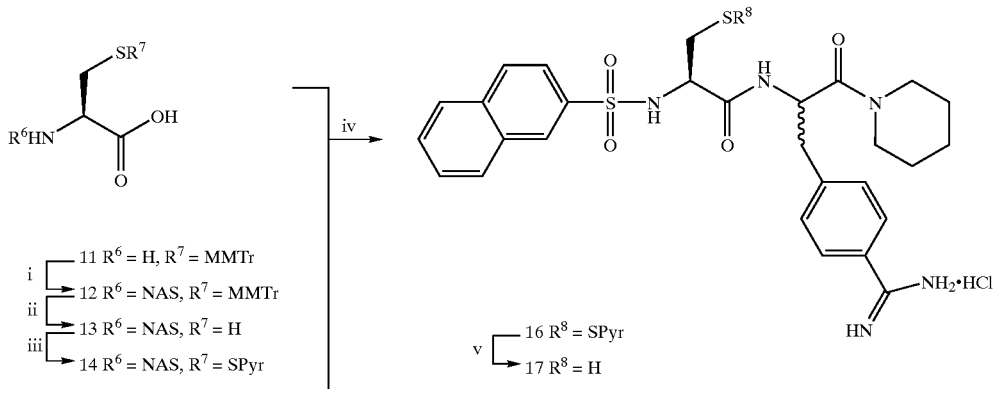
FORMULA SHEET 3
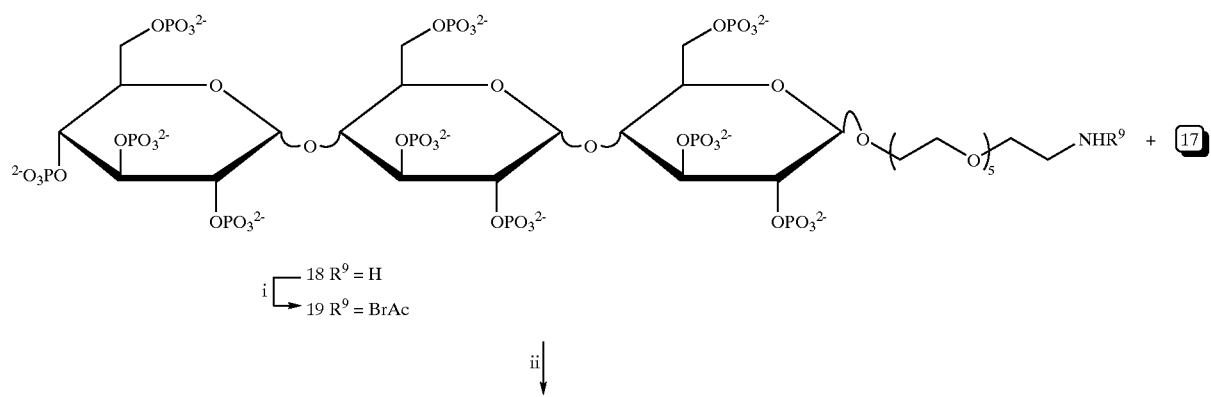

-continued
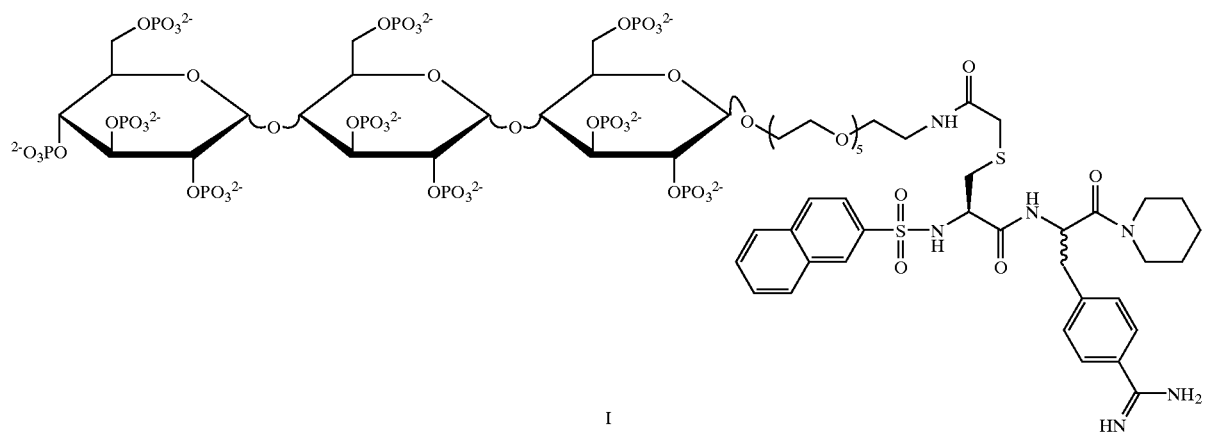
I
FORMULA SHEET 4
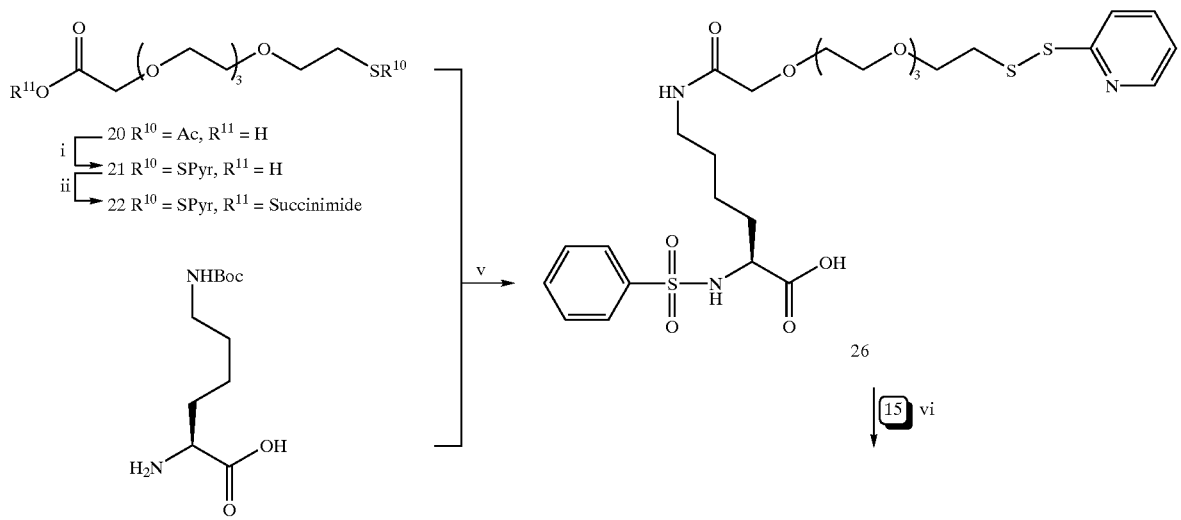
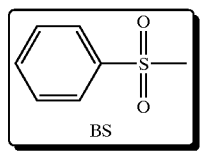
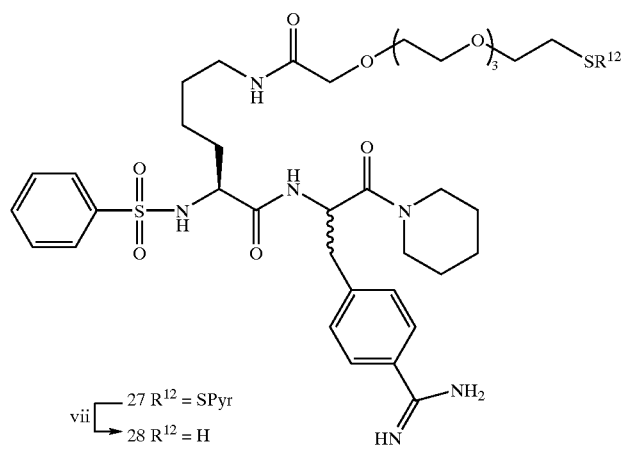

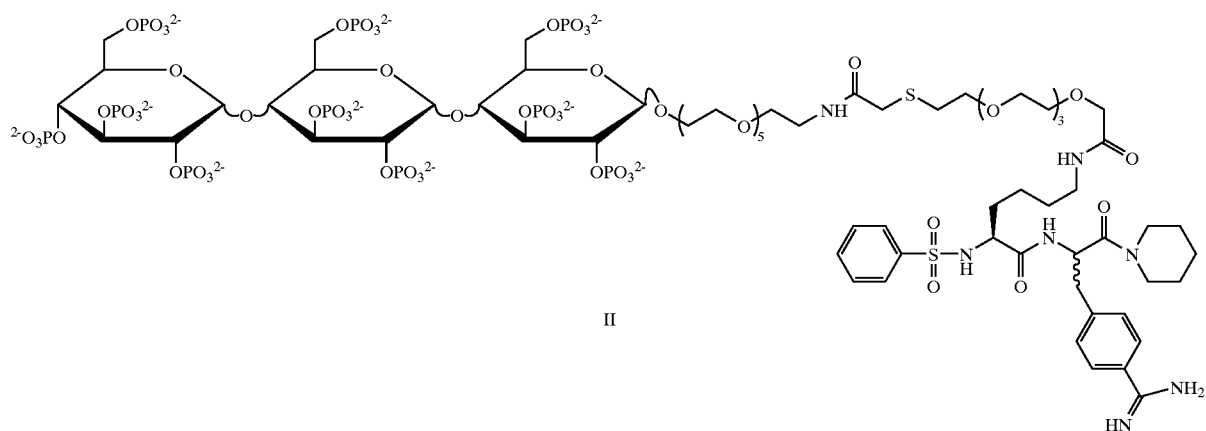
II
FORMULA SHEET 5
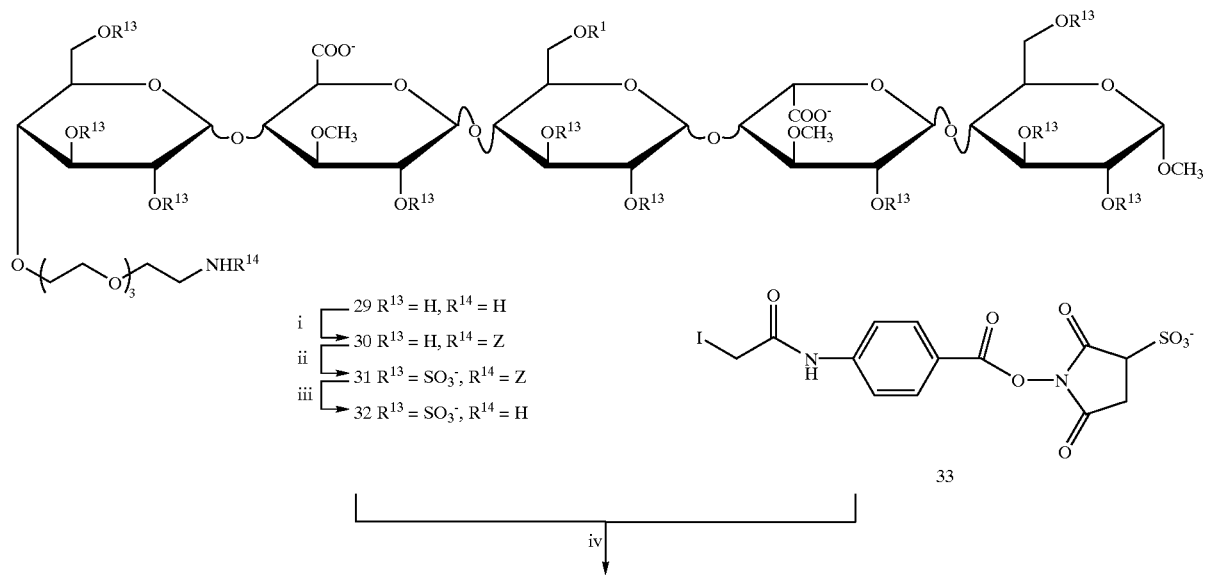
- i → 29 R[13] = H, R[14] = H
- ii → 30 R[13] = H, R[14] = Z
- iii → 31 R[13] = SO$_3^-$, R[14] = Z
- → 32 R[13] = SO$_3^-$, R[14] = H
33
iv
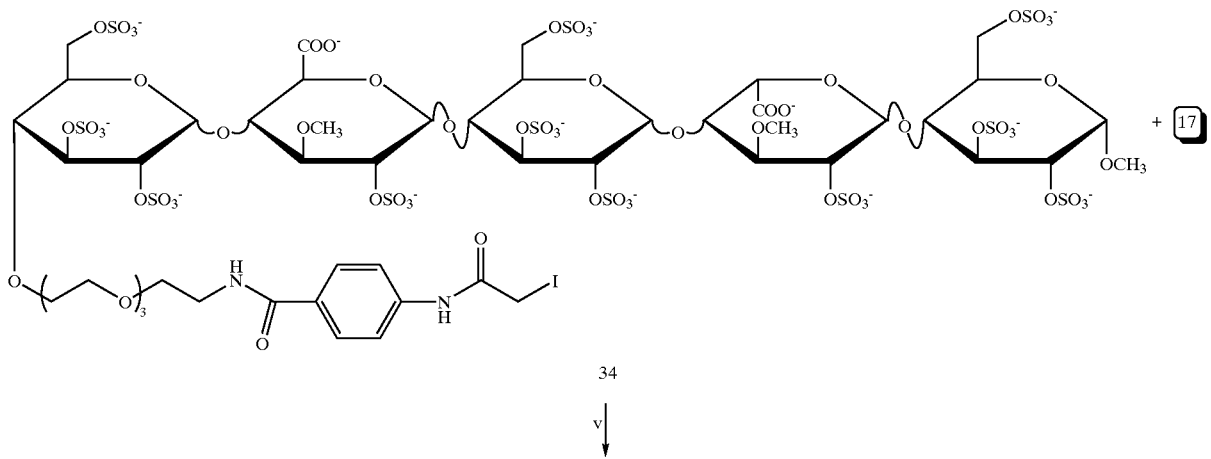
34
v

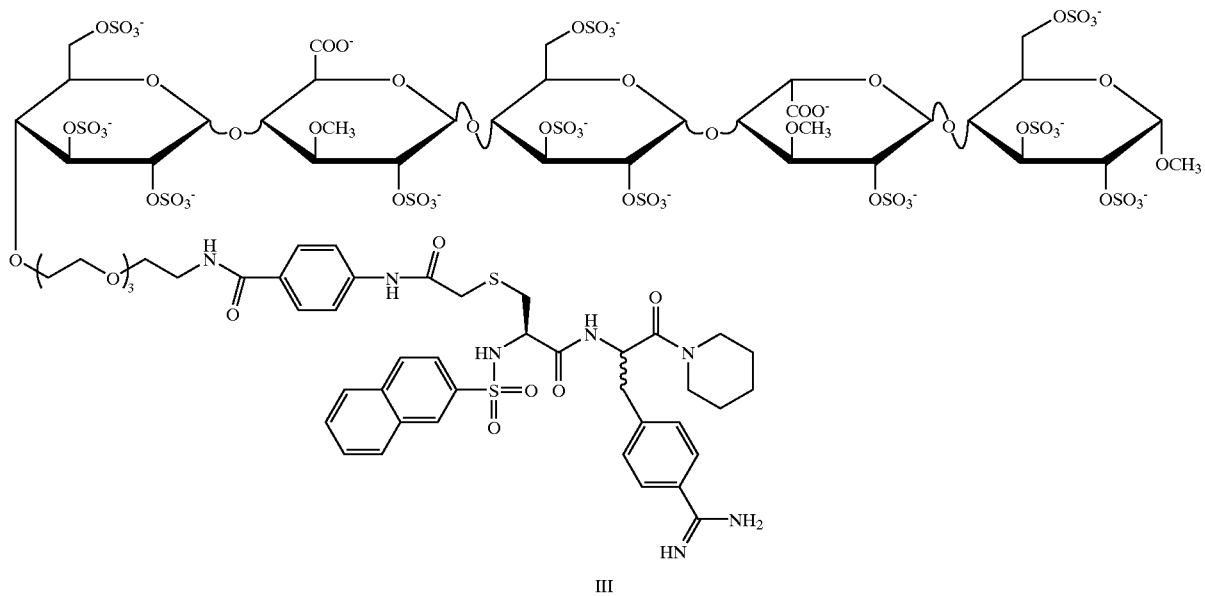

III

What is claimed is:

1. A compound of the formula (I)

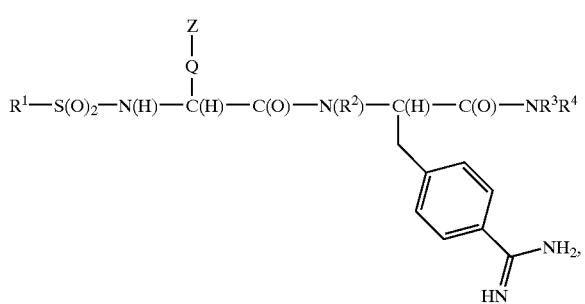

wherein

R¹ is phenyl, naphthyl, 1,2,3,4-tetrahydronaphthyl, (iso)quinolinyl, tetrahydro(iso)quinolinyl, 3,4-dihydro-1H-isoquinolinyl, chromanyl or the camphor group, which groups may optionally be substituted with one or more substituents selected from (1–8C)alkyl or (1–8C)alkoxy;

$R^2$ and $R^3$ are independently H or (1–8C)alkyl;

$R^4$ is (1–8C)alkyl or (3–8C)cycloalkyl;

or $R^3$ and $R^4$ together with the nitrogen atom to which they are bonded are a nonaromatic (4–8)membered ring optionally containing another heteroatom, the ring optionally being substituted with (1–8C)alkyl or $SO_2$-(1–8C)alkyl;

Q is a spacer having a chain length of 10 to 70 atoms; and

Z is a negatively charged oligosaccharide residue comprising two to six monosaccharide units, the charge being compensated by positively charged counterions;

or a pharmaceutically acceptable salt thereof or a prodrug thereof.

2. The compound of claim 1, wherein Z is derived from an oligosaccharide which has AT-III mediated anti-Xa activity.

3. The compound of claim 2, wherein Z is a pentasaccharide residue.

4. The compound of claim 3, wherein Z has the formula (II)

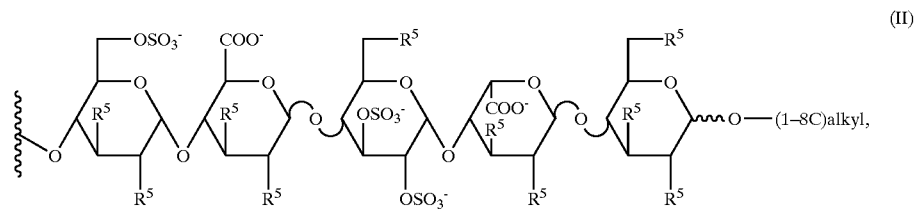

wherein $R^5$ is independently $OSO_3^{-1}$ or (1–8C)alkoxy.

5. The compound of claim 1, wherein $R^1$ is is phenyl, 4-methoxy-2,3,6-trimethylphenyl or naphthyl; $R^2$ is H; and $NR^3R^4$ represents the piperidinyl group.

6. The compound of claim 1, wherein Q has the formula (III)

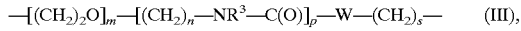

wherein

W is

—[1,4-phenylene-$NR^3$—C(O)]$_q$—$(CH_2)_r$—S— or —$(CH_2)_t$—S—$(CH_2)_u$—[O$(CH_2)_2$]$_v$—O—$(CH_2)_w$—C(O)—$NR^3$—;

and $R^3$ is independently H or (1–8C)alkyl;

m=1–12; n=1–8; p=0–4; q=0 or 1; r=1–8; s=1–8; t=1–8; u=1–8; v=1–12; w=1–8; the total number of atoms is 10–70; and the moiety —[(CH$_2$)$_2$O]$_m$— is the end with which Q is attached to Z.

7. The compound of claim 6, wherein Q is selected from

—[(CH$_2$)$_2$O]$_5$—(CH$_2$)$_2$—NH—C(O)—CH$_2$—S—CH$_2$—;

—[(CH$_2$)$_2$O]$_5$—(CH$_2$)$_2$—NH—C(O)—CH$_2$—S—(CH$_2$)$_2$—[O(CH$_2$)$_2$]$_3$—O—CH$_2$—C(O)—NH—(CH$_2$)$_4$—; and —[(CH$_2$)$_2$O]$_3$—(CH$_2$)$_2$—NH—C(O)-1,4-phenylene-NH—C(O)—CH$_2$—S—CH$_2$—.

8. A pharmaceutical composition comprising the compound of claim 1 and a pharmaceutically acceptable auxiliary.

9. A method of anti-thrombin therapy comprising administering an effective amount of a compound according to claim 1.

* * * * *